United States Patent [19]

Negrelli et al.

[11] Patent Number: 5,712,895
[45] Date of Patent: Jan. 27, 1998

[54] ROTATIONAL DIGITAL SUBTRACTION ANGIOGRAPHY PHANTOM

[75] Inventors: Donald E. Negrelli, Gates Mills; Hung Y. Wong, Solon, both of Ohio

[73] Assignee: Picker International, Inc., Highland Heights, Ohio

[21] Appl. No.: 783,503

[22] Filed: Jan. 14, 1997

[51] Int. Cl.$^6$ .................................................. G01D 18/00
[52] U.S. Cl. .................................................. 378/207; 378/4
[58] Field of Search ........................................ 378/4, 207

[56] References Cited

U.S. PATENT DOCUMENTS

| | | | |
|---|---|---|---|
| 5,225,979 | 7/1993 | Feldman et al. | 378/207 |
| 5,301,220 | 4/1994 | Wong | 348/162 |
| 5,442,674 | 8/1995 | Picard et al. | 378/20 |

*Primary Examiner*—Don Wong
*Attorney, Agent, or Firm*—Fay, Sharpe, Beall, Fagan, Minnich & McKee

[57] ABSTRACT

A gantry (18) that carries an x-ray source (14) and an x-ray detector (16) rotates around a test phantom (10) in a forward direction. A plurality of forward projection images are generated and stored in a forward image memory (42). The angle at which each forward direction projection image is generated is stored in a position memory (56). The gantry is then rotated in a reverse direction and a reverse direction image is generated at generally the same angular positions as in the forward rotation direction. The forward and reverse direction projection images of the phantom are analyzed to determine an offset or error between each corresponding forward and reverse angular image position. The offsets are stored in an angular position look-up table (80) and a pixel reregistration look-up table (82). In subsequent reverse scans, the angular position at which the reverse direction projection images are taken are altered in accordance with the angular offset for the corresponding angular position. The forward sweep images are video pixel position shifted in accordance with the video pixel offset for the corresponding angular position to bring the forward and reverse direction projection images into registration.

23 Claims, 6 Drawing Sheets

ROTATIONAL DIGITAL SUBTRACTION ANGIOGRAPHY PHANTOM

BACKGROUND OF THE INVENTION

The present invention relates to the radiographic examination arts. It finds particular application in conjunction with calibrating a Rotational Digital Subtraction Angiography ("DSA") system during setup and will be described with particular reference thereto. It will be appreciated, however, that the invention will also find application in other rotational angiography systems, and the like.

Heretofore, conventional DSA has been used for imaging blood vessels or blood flow. Blood vessels are made visible in x-ray images by means of a contrast media injected into the bloodstream. Visibility of the blood vessels is enhanced by the subtraction of digital TV images taken at different times—one image is taken when the blood is opacified with contrast media (called the contrast or dye image) and the second image is taken when the blood is not opacified (called the mask image). The two images are superimposed and subtracted pixel-by-pixel to produce an image of the blood vessels without showing other body structures such as bone, which are subtracted out. Dynamics of blood flow are visualized through playback of a series of subtracted images taken at a predetermined frame rate.

In conventional DSA, the imaging system remains fixed with respect to the patient during the acquisition of images. By distinction, Rotational DSA is the technique for acquiring angiographic images while the imaging system rotates around the patient. Conventionally, two half rotation data acquisitions are conducted. One rotation is made with contrast media injected into the subject. The other rotation, made in the opposite rotational direction, is made with no contrast media. Ideally, each subtracted image is produced from a contrast image and its corresponding mask image, both taken at precisely the same imaging system rotational angle. However, in point of fact, there is normally an offset between the supposed same image position during the mask image and a corresponding contrast image. The accuracy of registration between the contrast image and the mask image is directly related to the deviation between the angles at which the contrast and mask images are acquired—the smaller the deviation between the two angles, the better the subtracted image is.

One disadvantage of Rotational DSA systems is the difficulty in obtaining registration between the mask images and the contrast images.

The present invention provides a new and improved calibration apparatus and method which overcomes the above-referenced problems and others.

SUMMARY OF THE INVENTION

In accordance with the present invention, a calibration system for a rotational digital subtraction angiography system is provided.

The calibration system includes a gantry and an x-ray source and x-ray detector mounted on the gantry on opposite sides of an examination region. The gantry rotates the x-ray source and detector in an arcuate path across the examination region. A test phantom, supported in the examination region, includes a block of x-ray transparent material, a plurality of x-ray opaque vertical indicia partially encircling the block, an x-ray opaque element located at an isometric center of the block and a plurality of x-ray opaque horizontal indicia radiating at an angular displacement from one another. The indicia correspond to a plurality of registration angles along the arcuate path around the block. An image of the element is projected on at least one of the indicia when the element is exposed to x-rays. The angular displacement represents a range of misalignment. The calibration system also includes a rotation control for rotating the gantry, x-ray source, and x-ray detector in a forward sweep rotation direction around the examination region and in a reverse sweep rotation direction around the examination region. A control for at least one of the x-ray source and x-ray detector generates a plurality of projection images of the test phantom at generally corresponding angular positions during the forward and reverse sweep rotations.

In accordance with a more limited aspect of the invention, the control includes the proper setup of the X-ray source to image distance, the proper setup of the image magnification, and the proper setup of the height and horizontal position of the table in relation to the gantry so that the gantry rotates symmetrically around the test pattern with a rotating center at precisely the isometric center of the test pattern.

In accordance with one aspect of the invention, the control includes a synchronous control for controlling the generation of projection images at a plurality of angular orientations in the forward sweep rotation direction. A memory stores the angular orientations at which projection images are generated in the forward sweep rotation direction. A comparator compares in the reverse sweep rotation direction, a current angular orientation with the angular orientations stored in the memory. An asynchronous control connected with the comparator triggers the taking of a projection image in response to the comparator indicating a matching of the stored and current angular positions. An angular offset look-up table is associated with one of the memory and the comparator. The control generates projection images in both the forward and reverse sweep rotation directions at corresponding angular positions. The angular offset look-up table provides an angular offset for each of the angular positions at which images are generated. Each angular offset indicates a coarse adjustment required for bringing the corresponding forward sweep rotation and reverse sweep rotation direction projection images into alignment.

In accordance with a yet another aspect of the invention, the calibration system includes an automatic calibration system for determining the angular offsets and/or pixel shifts loaded into the angular offset look-up table. A pixel reregistration processor loads and applies pixel reregistration offsets to the projection images. Each pixel offset indicates a fine adjustment required for bringing the corresponding acquired forward sweep rotation and reverse sweep rotation direction projection images into alignment. The calibration system further includes a pixel reregistration look-up table associated with one of the memory and the pixel reregistration processor. The pixel reregistration look-up table stores, for each of the angular positions at which the projection images are generated, the pixel reregistration offsets. The calibration system further includes a subtraction/overlay circuit for generating a subtracted image between the forward sweep rotation image and the corresponding reverse sweep rotation image and a pixel shift/angular position offset calculator. The calculator estimates one of the angular offset and the pixel reregistration offset, at each corresponding angular position of the subtracted image and performs numerical and statistical operations. The statistical operations include determining the offset and translating and storing the offset into at least one of the angular position offset look-up table and the pixel reregistration offset look-up table.

One advantage of the present invention is that it simplifies the process of calibrating and setting up rotational DSA acquisition systems.

Another advantage is that it facilitates automated set-up.

Another advantage is that it improves registration between mask and contrast images.

Another advantage is that it provides a qualitative tool to quantify the accuracy of the rotational DSA acquisition systems. One benefit of this is to provide direct visual determination of the quality of the system during manufacturing control process or periodic maintenance check up.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
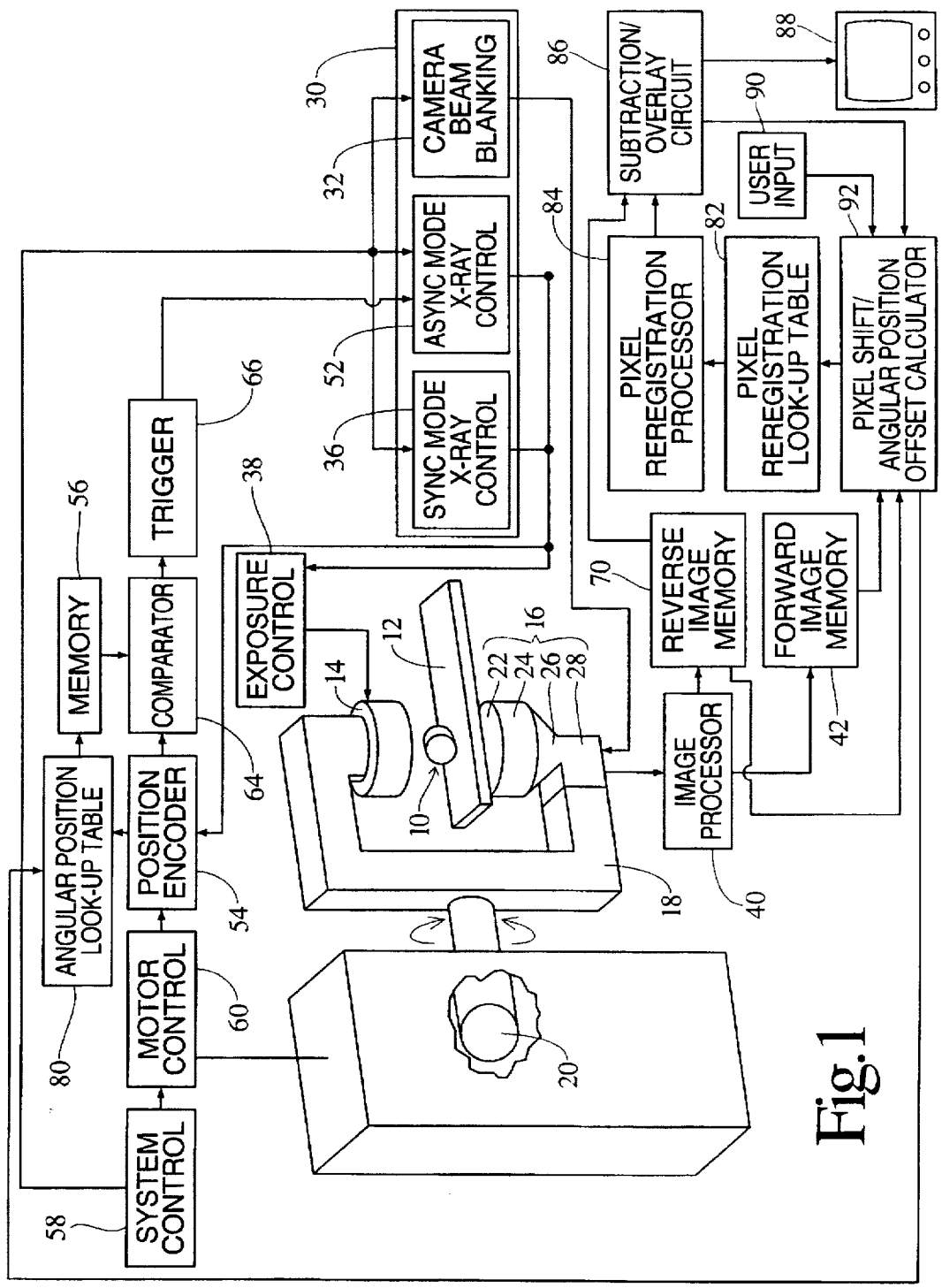
FIG. 1 is a diagrammatic illustration of a rotational digital subtraction angiography system which is calibrated with a test phantom in accordance with the present invention.

With reference to FIG. 1, a test phantom 10 is supported on a subject couch or support 12 for calibrating an x-ray source 14 and an x-ray detector assembly 16. The x-ray source 14 is controlled electronically to stop and start the generation of x-rays.

The x-ray source 14 and detector 16 are mounted on a gantry 18 for rotational movement around the test phantom 10. A motor 20 rotates the gantry 18 at a selected rate.

The radiation detector assembly 16 includes a phosphor plate or sheet 22 disposed behind an optically opaque but radiation transparent shield. The phosphor converts received radiation into a relatively faint optical image. Preferably, the phosphor is part of an image intensifier 24 that boosts the intensity of the optical image. A lens system 26 focuses the intensified optical image onto the image pick-up surface of a camera 28. Preferably, the camera 28 is a video camera that produces video signals. Beam blanking of the video camera 28 is controlled by a timing and control circuit 30 having a video camera beam blanking control 32. In beam blank mode, the camera is held at ready to acquire images and starts to produce an image in response to an external beam un-blank signal. Alternatively, other opto-electrical converters can be utilized to convert the optical image into an electronic image representation.

To calibrate the x-ray source 14, detector 16 and gantry assembly in the preferred embodiment with the x-ray source to image distance and image magnification properly set, the test pattern support height and horizontal position are set so that the gantry rotates around the test phantom 10. The rotational center of the gantry 18 is located at the isometric center of the test phantom 10. Reference images are first collected at a plurality of positions during a forward sweep of the x-ray source 14 and x-ray detector assembly 16 around the test phantom 10. X-rays originate at the x-ray source 14, pass through the phantom 10, and are received by the detector assembly 16. The x-ray source 14 and x-ray detector assembly 16 are preferably rotated at a rate of about 30 degrees per second. Of course, other speeds, such as 25 degrees per second, can also be selected. On the forward sweep, a synchronous control 36 triggers an exposure control 38 to cause exposures at regular time intervals. An image processor 40 processes the video camera output from each exposure to generate a series of reference images. A forward image memory 42 stores each reference image.

Figure 2:
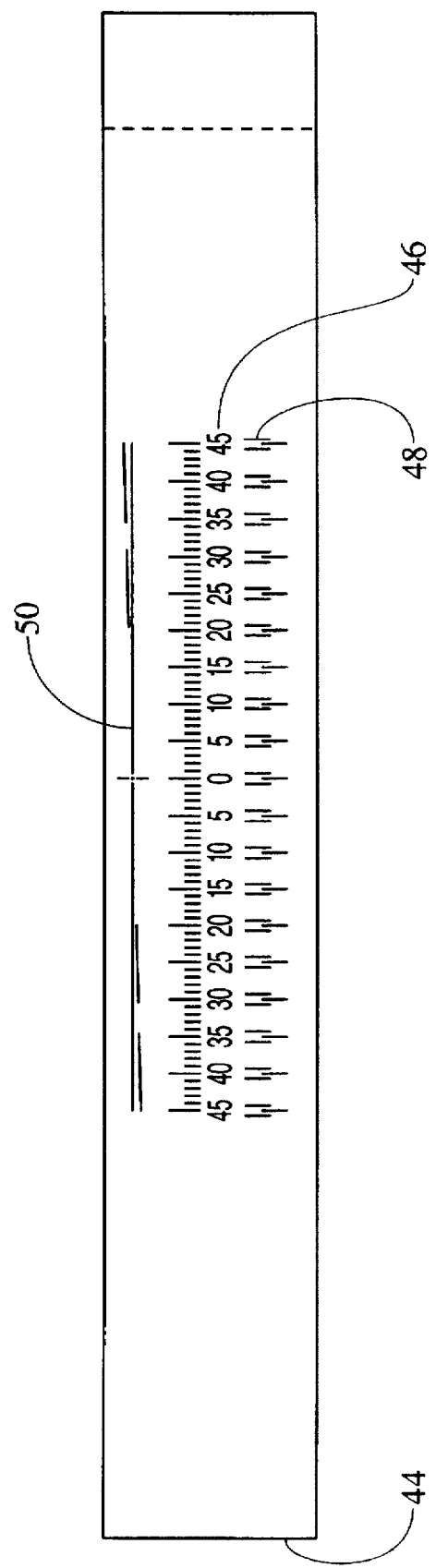
FIG. 2 illustrates an x-ray opaque gauging portion of the test phantom opened out flat.

With reference to FIG. 2, each reference image of the phantom 10 contains images of a radiation opaque gauge 44. The gauge 44 includes numerical indicia 46, along with indicia consisting of staggered lines in the vertical direction 48 and horizontal lines 50 at a small angular displacement from one another. The reference image also contains an image of a metal pin 52, located at an isometric center of the phantom 10 (see FIG. 3), projected on the numerical indicia 46. The projected image of the pin 52 on the numerical indicia 46 indicates an angular location of the x-ray source 14 and x-ray detector 16 relative to the test phantom 10 at each exposure. The indicia 46, 48, 50 and pin 52 are formed from x-ray opaque material.

A position or angular orientation determining device 54, such as an optical encoder, a linear rheostat, or the like, is enabled and reads the angular position of the gantry at a terminal end of each exposure. The synchronous mode control 36, within the timing and control circuit 30, communicates with the position encoder 54 to determine the angular position of the gantry at the terminal end of each exposure. Each terminal end angle is recorded in a position memory 56.

When the gantry 18 has completed its forward sweep around the test phantom 10, a system control 58 then causes a motor control 60 to commence a reverse sweep (i.e., rotate the gantry 18 in the opposite direction). During the reverse sweep, the gantry 18 preferably rotates at substantially the same speed that it rotated in the forward sweep. The system control 58 then enables an asynchronous mode control portion 62 of the timing and control circuit 30.

During the reverse sweep, a comparator 64 compares the current position of the gantry from the position encoder 54 with the terminal positions stored in the position memory 56. Each time the gantry moving in the reverse direction reaches one of the stored angular positions, a trigger circuit 66 causes the asynchronous mode x-ray exposure controller 62 to initiate an x-ray exposure. The acquired image is processed in the image processor 40 and stored in a reverse sweep image memory 70.

Figure 4:
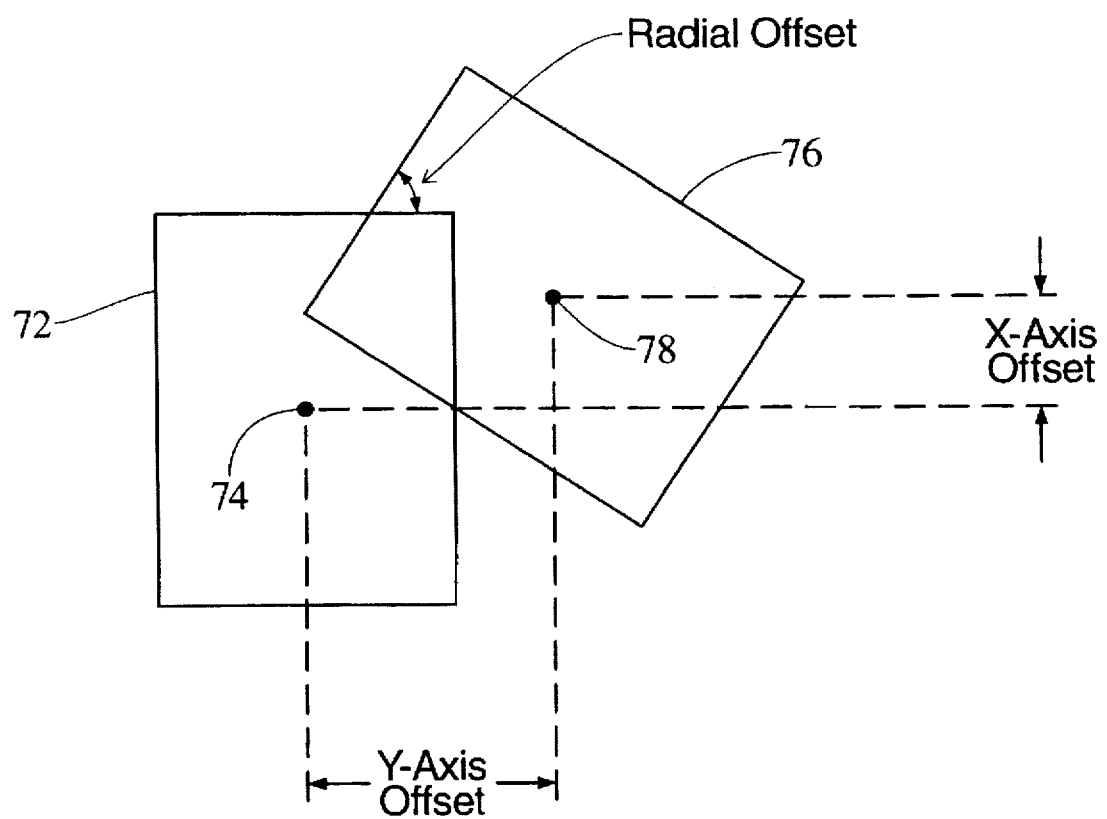
FIG. 4 illustrates different types of image misalignments.

As explained above, in the background of the invention section, the forward and reverse sweep images typically are out of alignment. FIG. 4 illustrates an example of an image misalignment. A forward image 72 includes a forward image center 74 at specific set of x and y coordinates. A reverse image 76 includes a reverse image center 78 at another specific set of x and y coordinates. Consequently, image misalignment may include an x-axis offset, a y-axis offset and/or a radial offset. The misalignment is due to various causes attributable to the mechanics of rotating the gantry 18, the precise mechanical position of the camera 28 at each of the image projection angular positions throughout the forward and reverse rotation sweeps, the electronics of triggering the x-ray source 14, the physics of initiating the x-ray transmission, and the like. Moreover, the misalignment differs from image to image.

The calibration procedure determines coarse and fine errors for each image angular position. The coarse error adjustment is stored in an angular position look-up table 80 and the fine error adjustment is stored in a pixel reregistration look-up table 82. In the preferred embodiment, the angular position look-up table 80 applies a corresponding coarse error adjustment to each angular position before it is stored in the position memory 56. Alternatively, the angular position look-up table 80 adjusts the positions read out of the memory 56 or the return sweep encoded positions read out from encoder 54. A pixel reregistration processor 84 applies the fine error adjustment stored in the pixel reregistration look-up table 82 by video pixel shifting each of the acquired forward sweep rotation images at each corresponding angular position. The video pixel shifted forward sweep images and the reverse sweep images are subtracted from each other at a subtraction/overlay circuit 86 and are displayed on a human-readable display device 88. Alternatively, the pixel reregistration processor 84 adjusts the video pixel positions of the reverse sweep rotation images.

To calculate the calibration factors manually, the images of the calibration phantom taken during the forward sweep and the reverse sweep are retrieved for each angular position. An operator views the calibration phantom image, taken during the forward sweep, on the human-readable display device 88. The operator notes the angle, indicated by the numerical indicia 46, through which the image of the metal pin 52 is projected. The offset for the angular position look-up table 80 is calculated by determining a difference between the forward and reverse angles noted on the numerical indicia 46. The operator then stores the offset, associated with the particular gantry position in the angular position look-up table 80. Alternatively, the forward sweep and the reverse sweep rotation images are subtracted from each other at each corresponding image projection angular position. The operator observes each of the subtracted images displayed on the display device 88. Next, using a user input device 90, such as a computer mouse or keyboard and like, the operator manually adjusts the video pixel position offset for each forward sweep image. This results in a least misaligned subtracted image for each of the corresponding angular positions. For each of the image projection angular positions, a pixel shift/angular position offset calculator 92 translates the amount of forward image video pixel position offset into a corresponding angular position adjustment and stores the result in the angular position look-up table 80. After the angular position offset is calculated for each angular position at which pictures are taken, the calibration process is repeated. If the image angles measured in the forward and reverse directions are not within a predetermined acceptable tolerance range, a video pixel position offset is calculated between the two images. More specifically, the offset required to produce a minimum misalignment in the subtracted image at each image projection angular position is stored into the pixel reregistration look-up table 82. Therefore, the previously stored angular position look-up table 80 and the newly stored pixel reregistration look-up table 82 together provide the coarse and fine error adjustments.

Figure 5A:
FIG. 5A illustrates overlaid images of the radiation opaque vertical line gauge which result when there is no offset between a position of an image taken during a forward sweep and an image taken during a reverse sweep.
Figure 6A:
FIG. 6A illustrates overlaid images of the radiation opaque horizontal line gauge which result when there is no offset between a position of an image taken during a forward sweep and an image taken during a reverse sweep.

With reference to FIG. 2, forward and reverse images of the vertical and horizontal indicia 48, 50 are generated and stored in the forward image memory 42 and the reverse image memory 70. A subtraction/overlay circuit 86 overlays or superimposes the forward and reverse images of the vertical and horizontal indicia 48, 50. If the images are precisely aligned, the marks on the indicia 48, 50 will overlay each other as illustrated in FIGS. 5A and 6A.

Figure 5B:
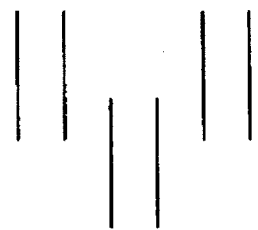
FIG. 5B illustrates overlaid images of the radiation opaque vertical line gauge which result when there is an axial offset of less than ½ degree between a position of an image taken during a forward sweep and an image taken during a reverse sweep.
Figure 5C:
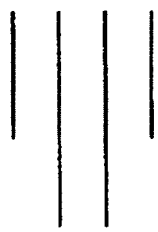
FIG. 5C illustrates overlaid images of the radiation opaque vertical line gauge which result when there is an axial offset of ½ degree between a position of an image taken during a forward sweep and an image taken during a reverse sweep.

On the other hand, if the two images are offset by the angular spacing between the vertical marks of indicia 48, ½ degree in the preferred embodiment, then the resultant image is as shown in FIG. 5C. That is, the low mark in the center of each image superimposes on the upper mark of the other image giving an apparent increase in the length of the center marks and an apparent increase in the number of marks.

Figure 5D:
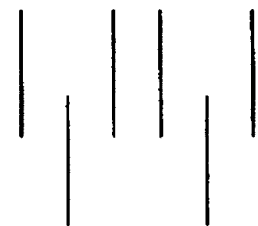
FIG. 5D illustrates overlaid images of the radiation opaque vertical line gauge which result when there is an axial offset of more than ½ degree but less than 1 degree between a position of an image during a forward sweep and an image taken during a reverse sweep.
Figure 5E:
FIG. 5E illustrates overlaid images of the radiation opaque vertical line gauge which result when there is an axial offset of 1 degree between a position of an image taken during a forward sweep and an image taken during a reverse sweep.

Analogously, for a 1 degree offset, the two superimposed sets of vertical indicia 48 are offset from each other by twice the inter mark spacing creating the pattern of FIG. 5E.

Figure 5F:
FIG. 5F illustrates overlaid images of the radiation opaque vertical line gauge which result when there is an axial offset of more than 1 degree between a position of an image taken during a forward sweep and an image taken during a reverse sweep.

FIG. 5B illustrates the indicia of two superimposed sets of vertical indicia 48 having an offset greater than zero and less than ½ degree. FIG. 5D illustrates the indicia of two superimposed sets of vertical indicia 48 having an offset greater than ½ degree and less than 1 degree. FIG. 5F illustrates the indicia of two superimposed sets of vertical indicia 48 having an offset greater than 1 degree.

Based on the image of the overlapped vertical indicia 48, the acceptable axial misalignment range is determined by the angular spacing between the low mark and the upper mark of the indicia 48 (½ degree in the preferred embodiment). Of course, different tolerance ranges can be specified by adjusting the angular spacing between marks.

Figure 6B:
FIG. 6B illustrates overlaid images of the radiation opaque horizontal line gauge which result when there is a radial offset of less than ½ degree between a position of an image taken during a forward sweep and an image taken during a reverse sweep.
Figure 6C:
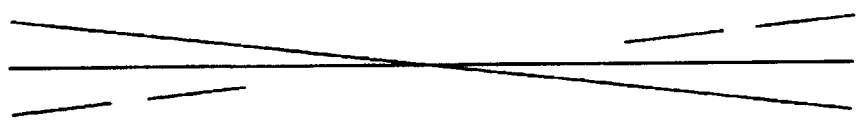
FIG. 6C illustrates overlaid images of the radiation opaque horizontal line gauge which result when there is a radial offset of ½ degree between a position of an image taken during a forward sweep and an image taken during a reverse sweep.
Figure 6D:
FIG. 6D illustrates overlaid images of the radiation opaque horizontal line gauge which result when there is a radial offset of more than ½ degree between a position of an image taken during a forward sweep and an image taken during a reverse sweep; and, FIG. 7 is a side view of the test phantom.

As an additional calibration check, the horizontal indicia markings 50 are also compared. When the phantom is perfectly orthogonal to the axis during both the forward and reverse rotation, the horizontal marks 50 are superimposed directly on each other in the overlaid image and equally disposed on opposite sides of the straight line (see FIG. 6A). However, when there is a radial angular offset in one of the forward and reverse sweeps relative to the phantom, the marks 50 will not overlay each other. Rather, the marks will be offset indicating that an adjustment to the gantry 18, and/or the pixel reregistration look-up table 82 should be made in order to line up the forward and reverse arcs precisely orthogonal to the central axis. FIGS. 6A, 6B and 6C illustrate characteristic patterns for different degrees of radial angle misalignment. FIG. 6B illustrates the indicia of two superimposed sets of horizontal indicia 50 having an offset less than ½ degree. FIG. 6C illustrates the indicia of two superimposed sets of horizontal indicia 50 having a ½ degree offset. FIG. 6D illustrates the indicia of two superimposed sets of horizontal indicia 50 having greater than a ½ degree offset.

In the preferred embodiment, the calibration is performed automatically. That is, when the pixel reregistration look-up table 82 set to a zero pixel shift, the images of the calibration phantom taken during the forward sweep are stored into the forward image memory 42, and the reverse sweep images are stored into the reverse image memory 70. The forward sweep image and corresponding reverse sweep image are subtracted from each other at each of the image projection angular positions. This subtraction is accomplished by analyzing the forward sweep image and the corresponding angular position reverse sweep image. The value of the image video pixel position offset due to misalignment is estimated and calculated by the pixel shift/angular position offset calculator 92. The pixel reregistration processor 84 applies the first estimated video pixel position offset to the forward sweep image and the statistical error of the pixel values of the subtracted image in comparison to the pixel values of a perfectly aligned and subtracted image is calculated. If the error falls within a predetermined range of tolerance the estimated video pixel position offset is translated into an angular position adjustment and stored into the angular position look-up table 80. Otherwise the video pixel position offset estimation is revised and applied to the forward sweep image until the statistical error of the pixel values of the subtracted image falls within the acceptable range of tolerance. This process is repeated for each of the angular positions at which pictures are taken. After the angular position offset is calculated for each image projection angular position, the calibration process is repeated. The video pixel position offset of each forward sweep image of the second calibration process is estimated, applied and revised to obtain a statistical error of the corresponding subtracted image to within the acceptable range specific to the second calibration process. The final video pixel position offset estimation is stored into the pixel reregistration look-up table 82 at corresponding angular position. This process is repeated until the pixel reregistration look-up table 82 is calibrated at each image projection angular position.

After calibration, similar forward and reverse images are generated with a patient on the patient support 12. The forward and reverse images are stored in the forward and reverse image memories 42 and 70. The image subtraction/overlay circuit 86 subtracts the forward and reverse images (i.e. the mask and contrast images) to create only an image of the circulatory system for display on the monitor 88.

Figure 3:
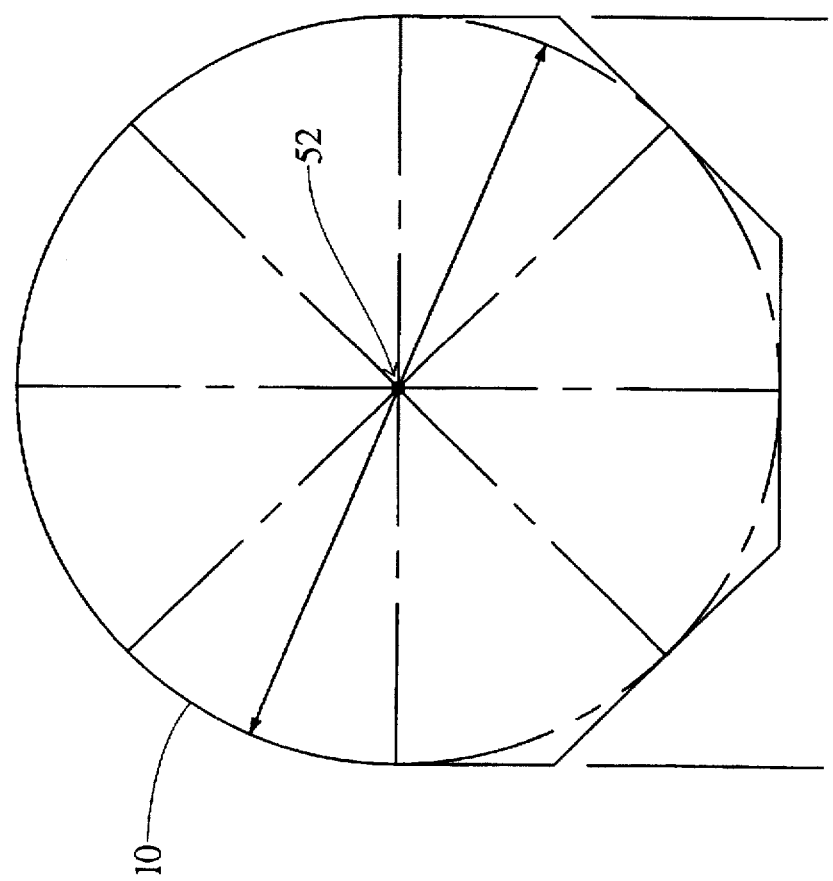
FIG. 3 is a front view of the test phantom.

FIG. 3 shows an end elevational view of the test phantom 10. The metal pin 52 is positioned at an isometric center of the phantom 10 and aligned with the rotational axis of the x-ray positioner.

Figure 7:
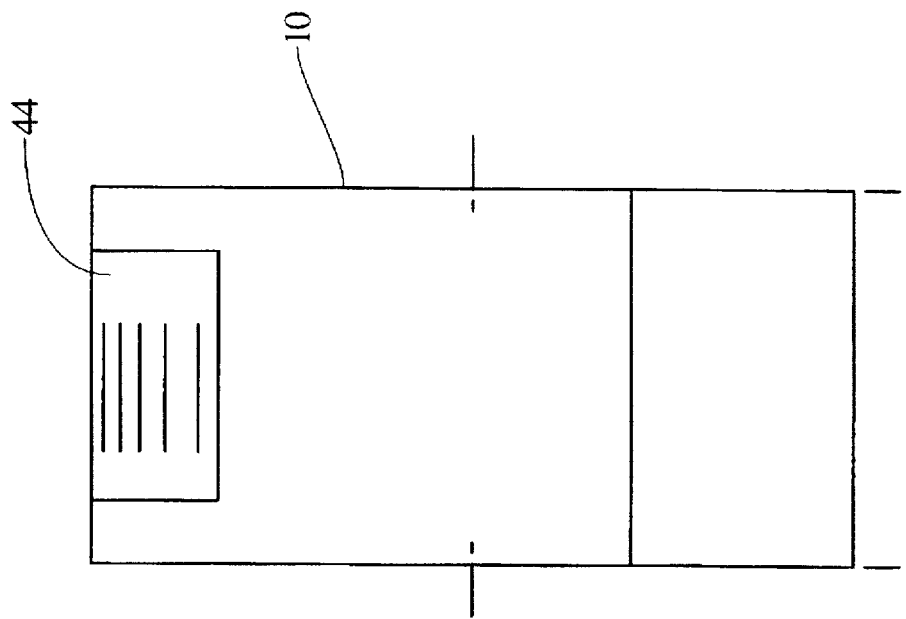

FIG. 7 illustrates a side elevational view of the phantom 10. The gauge 44, which contains the x-ray opaque indicia 46, 48, 50, is wrapped around the top side of the phantom 10.

The phantom 10 preferably has a polythene foam block in the shape of a cylinder with a circular arc segment over 90 degrees of the curved surface. The phantom 10 has flat surfaces on the side of the cylinder opposite from the gauge 44 for holding the phantom 10 steady on the table 12.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A calibration system for a rotational subtraction angiography system, the calibration system comprising:
   a gantry;
   an x-ray source and x-ray detector mounted on the gantry on opposite sides of an examination region, the gantry rotating the x-ray source and detector in an arcuate path around the examination region;
   a test phantom supported in the examination region, the test phantom including:
   a block of x-ray transparent material;
   a plurality of x-ray opaque vertical indicia partially encircling the block, the indicia corresponding to a plurality of registration angles along the arcuate path around the block;
   an x-ray opaque element located at an isometric center of the block, an image of the element being projected on at least one of the indicia when the element is exposed to x-rays; and,
   a plurality of x-ray opaque horizontal indicia radiating at an angular displacement from one another, the angular displacement representing a range of misalignment;
   a rotation control for rotating the gantry, x-ray source, and x-ray detector in a forward sweep rotation direction around the examination region and in a reverse sweep rotation direction around the examination region; and,
   a control for at least one of the x-ray source and x-ray detector for generating a plurality of projection images of the test phantom at generally corresponding angular positions during the forward and reverse sweep rotations.

2. The calibration system as set forth in claim 1 wherein the control includes:
   a synchronous control for controlling the generation of projection images at a plurality of angular orientations in the forward sweep rotation direction;
   a memory for storing the angular orientations at which projection images are generated in the forward sweep rotation direction;

a comparator for comparing, in the reverse sweep rotation direction, a current angular orientation with the angular orientations stored in the memory;

an asynchronous control connected with the comparator for triggering the taking of a projection image in response to the comparator indicating a matching of the stored and current angular positions, for generating projection images in both the forward and reverse sweep rotation directions at corresponding angular positions; and, an angular offset look-up table associated with one of the memory and the comparator, the angular offset look-up table providing an angular offset for each of the angular positions at which images are generated, each angular offset indicating a coarse adjustment required for bringing the corresponding forward sweep rotation and reverse sweep rotation direction projection images into alignment.

3. The calibration system as set forth in claim 2 further including:

an automatic calibration system for determining the angular offsets loaded into the angular offset look-up table;

a pixel reregistration processor for loading and applying pixel reregistration offsets to the projection images, each pixel offset indicating a fine adjustment required for bringing the corresponding acquired forward sweep rotation and reverse sweep rotation direction projection images into alignment;

a pixel reregistration look-up table associated with one of the memory and the pixel reregistration processor, the pixel reregistration look-up table storing, for each of the angular positions at which the projection images are generated, the pixel reregistration offsets;

a subtraction/overlay circuit for generating a subtracted image between the forward sweep rotation image and the corresponding reverse sweep rotation image; and, a pixel shift/angular position offset calculator for estimating one of the angular offset and the pixel reregistration offset, at each corresponding angular position of the subtracted image, the calculator performing numerical and statistical operations, determining the offset, and translating and storing the offset into at least one of the angular position offset look-up table and the pixel reregistration offset look-up table.

4. The calibration test system as set forth in claim 3, wherein the vertical indicia have:

a first characteristic test pattern when the indicia are precisely superimposed in the superimposed forward and reverse sweep rotation direction images;

a second characteristic pattern when the indicia are offset by a first axial offset in the superimposed forward and reverse sweep rotation direction images;

a third characteristic pattern when the indicia are offset by a second selected axial orientation in the superimposed forward and reverse sweep rotation direction images;

a fourth characteristic pattern when the indicia are offset by a third selected axial orientation in the superimposed forward and reverse sweep rotation direction images;

a fifth characteristic pattern when the indicia are offset by a fourth selected axial orientation in the superimposed forward and reverse sweep rotation direction images;

a sixth characteristic pattern when the indicia are offset by a fifth selected axial orientation in the superimposed forward and reverse sweep rotation direction images;

wherein horizontal indicia have:

a first characteristic test pattern when the indicia are precisely superimposed in the superimposed forward and reverse sweep rotation direction images;

a second characteristic pattern when the indicia are offset by a first radial offset in the superimposed forward and reversed sweep rotation direction images;

a third characteristic pattern when the indicia are offset by a second selected radial orientation in the superimposed forward and reversed sweep rotation direction images; and, a fourth characteristic pattern when the indicia are offset by a third selected radial orientation in the superimposed forward and reversed sweep rotation direction images; and, wherein the characteristic patterns of the vertical and horizontal indicia of the superimposed images indicate a visual indication of a level of misalignment between the forward sweep image and corresponding reverse sweep image, the level of misalignment indicating whether the rotational subtraction angiography system is within an acceptable tolerance.

5. The calibration system as set forth in claim 4 wherein the vertical indicia include sets of staggered lines in an axial direction.

6. The calibration system as set forth in claim 4 wherein the horizontal indicia include radiated lines in a transverse direction.

7. The calibration system as set forth in claim 1 wherein the vertical indicia include numerical indicia representative of the generally corresponding angular positions during the forward and reverse sweep rotations at which the x-rays expose the element.

8. The calibration system as set forth in claim 1 wherein the vertical indicia lie along a circular arc segment.

9. A test phantom for calibrating a rotational subtraction angiography system, the test phantom comprising:

a block of x-ray transparent material;

a plurality of x-ray opaque first indicia on the block, each first indicia corresponding to an angle in an arcuate path around the block;

an x-ray opaque pin located at an isometric center of the block, an image of the pin being projected on at least one of the first indicia when x-rays pass through the block; and, a plurality of x-ray opaque second indicia on the block, each second indicia corresponding to a predetermined radial angle transversing the block.

10. The test phantom as set forth in claim 9 wherein the first indicia include numerical indicia representative of the angle at which the x-rays expose the pin.

11. The test phantom as set forth in claim 9 wherein the indicia include groups of vertical marks offset from each other in one dimension, the offset vertical marks having:

a first pattern in aligned superimposed images;

a second pattern in the aligned superimposed images offset by a first offset angle;

a third pattern in the aligned superimposed images offset by a second offset angle;

a fourth pattern in the aligned superimposed images offset by a third offset angle;

a fifth pattern in the aligned superimposed images offset by a fourth offset angle; and, a sixth pattern in the aligned superimposed images offset by a fifth offset angle.

12. The test phantom as set forth in claim 11 wherein the offset vertical marks include groups of staggered lines.

13. The test phantom as set forth in claim 12 wherein the lines are equally spaced.

14. The test phantom as set forth in claim 9 wherein the second indicia includes horizontal lines offset from each other and have:

a first pattern in aligned superimposed images;

a second pattern in the aligned superimposed images having an offset of a first radial offset angle;

a third pattern in the aligned superimposed images having an offset of a second radial offset angle; and, a fourth pattern in the aligned superimposed images having an offset of a third radial offset angle.

15. The test phantom as set forth in claim 14 wherein the horizontal lines are transverse the surface of the block.

16. A method for calibrating a rotational subtraction x-ray system, the method comprising:

placing a test phantom within an examination region on a test pattern support, the test phantom including a plurality of radiation opaque indicia;

setting an x-ray source to image distance and an image magnification to predetermined values;

setting height and horizontal positions of the test pattern support so that the gantry rotates around the test phantom, the gantry having a rotating center at an isometric center of the test phantom;

rotating an x-ray source and an x-ray detector around the examination region in a first direction for generating a first plurality of projection images of the radiation opaque indicia at each of a first plurality of angular image positions;

rotating the x-ray source and the x-ray detector around the examination region in an opposite direction for generating a second plurality of projection images of the indicia at each of a second plurality of angular image positions, each of the second plurality of angular image positions generally corresponding to, and being offset from, one of the first plurality of angular image positions; and, analyzing the first plurality of projection images and the second plurality of projection images for determining a first offset between each of the generally corresponding first plurality of angular image positions and second plurality of angular image positions.

17. The method for calibrating a rotational subtraction x-ray system according to claim 16, wherein the analyzing step includes:

applying the first offset to the corresponding image of the forward sweep memory by shifting pixel positions of the image;

subtracting the shifted pixel position image from the corresponding reverse sweep rotation image for generating a subtracted image;

calculating a statistical error of pixel values of the subtracted image relative to pixel values of an aligned subtracted image;

comparing the statistical error with a predetermined range of acceptable limits, translating the first offsets into angular position offsets and storing the angular position offsets into an angular position look-up table; and, recalculating the first offsets and repeating the analyzing step if the statistical error exceeds the predetermined range of acceptable limits.

18. The method for calibrating a rotational subtraction x-ray system according to claim 16, wherein the analyzing step includes:

based on an offset between one angular image position of the first plurality of angular image positions and second plurality of angular image positions, interpolating the remainder of the first offsets.

19. The method for calibrating a rotational subtraction x-ray system according to claim 17 further including:

rotating the x-ray source and the x-ray detector around the examination region in the first direction to generate a third plurality of projection images of the radiation opaque indicia including a plurality of patterns, near each of the first plurality of angular image positions;

rotating the x-ray source and the x-ray detector around the examination region in the opposite direction to generate a fourth plurality of projection images of the indicia, including the plurality of patterns, near each of the plurality of angular image positions adjusted with the first offsets; and, analyzing the third plurality of projection images and the fourth plurality of projection images for determining a second offset between each of the generally corresponding third plurality of angular image positions and fourth plurality of angular image positions.

20. The method for calibrating a rotational subtraction x-ray system according to claim 19, wherein the second analyzing step includes:

applying the second offsets to the corresponding third image of the forward image memory by shifting pixel positions of the third image;

subtracting the shifted pixel position image from the corresponding reverse sweep rotation image to generate a second subtracted image;

calculating a second statistical error of the pixel values of the second subtracted image relative to pixel values of a second aligned subtracted image;

comparing the second statistical error with the predetermined range of acceptable limits, translating the second offsets into angular position offsets and storing the second angular position offsets into a pixel reregistration look-up table; and, recalculating the second offsets and repeating the second analyzing step if the second statistical error exceeds the predetermined range of acceptable limits.

21. The method for calibrating a rotational subtraction x-ray system according to claim 20, wherein the second analyzing step includes:

based on an offset between one angular image position of the third plurality of angular image positions and fourth plurality of angular image positions, interpolating the remainder of the second offsets.

22. The method for calibrating a rotational subtraction x-ray system according to claim 17, wherein the analyzing step is manually performed and includes:

shifting pixel positions for the forward sweep image through a user input device such as computer mouse;

observing the subtracted image superimposed with the corresponding angular position reverse sweep image on the human readable display device, continuously adjusting the pixel position of the forward image until the subtracted image shows a least amount of misalignment; and, translating and storing current pixel position offsets of the forward sweep image into the angular position look-up table.

23. The method for calibrating a rotational subtraction x-ray system according to claim 20, wherein the second analyzing step is manually performed and includes:

shifting pixel positions for the forward sweep image through a user input device such as computer mouse;

observing the second subtracted image superimposed with the corresponding angular position reverse sweep image on the human readable display device, continuously adjusting the pixel position of the forward image until the second subtracted image shows a least amount of misalignment; and, translating and storing current pixel position offsets of the forward sweep image into the pixel reregistration look-up table.

* * * * *